United States Patent [19]

Bartelt et al.

[11] Patent Number: 4,895,154
[45] Date of Patent: Jan. 23, 1990

[54] ELECTRONIC STIMULATING DEVICE FOR ENHANCED HEALING OF SOFT TISSUE WOUNDS

[75] Inventors: James T. Bartelt; Alan R. Owens, both of Longmont, Colo.

[73] Assignee: Staodynamics, Inc., Longmont, Colo.

[21] Appl. No.: 159,863

[22] Filed: Feb. 19, 1988

[51] Int. Cl.⁴ ................................................ A61N 1/00
[52] U.S. Cl. ..................................... 128/421; 128/422; 128/423 R
[58] Field of Search ................... 128/419 R, 421, 422, 128/423 R, 783

[56] References Cited

U.S. PATENT DOCUMENTS

| | | | |
|---|---|---|---|
| 4,312,340 | 1/1982 | Donadelli | 128/421 |
| 4,580,570 | 4/1986 | Sarrell et al. | 128/421 |
| 4,582,063 | 4/1986 | Mickiewicz et al. | 128/421 |
| 4,712,558 | 12/1987 | Kidd et al. | 128/421 |
| 4,769,881 | 9/1988 | Pedigo et al. | 128/421 |

Primary Examiner—Francis Jaworski
Assistant Examiner—George Manuel
Attorney, Agent, or Firm—Robert E. Harris

[57] ABSTRACT

An electronic stimulating device for wound healing and, more particularly, for enhancing healing of soft tissue wounds. The device includes a plurality of signal generators for generating output pulses suitable for enhancing healing of soft tissue wounds by application of the output pulses through electrodes to the soft tissue to be healed. Two pairs of active electrodes are included along with a pair of return electrodes. Control signals from a pulse generator control generation of the output pulses and a digital timer is included for causing treatmet for a predetermined period of time. The intensity, polarity, and rate of the output pulses can be varied by rotation of control knobs on the front panel of the device or, alternately, can be effected by a series of switches located on the front panel of the device, with varying intensities of output being indicated by brightness varying light emitting diodes.

20 Claims, 4 Drawing Sheets

Fig_1

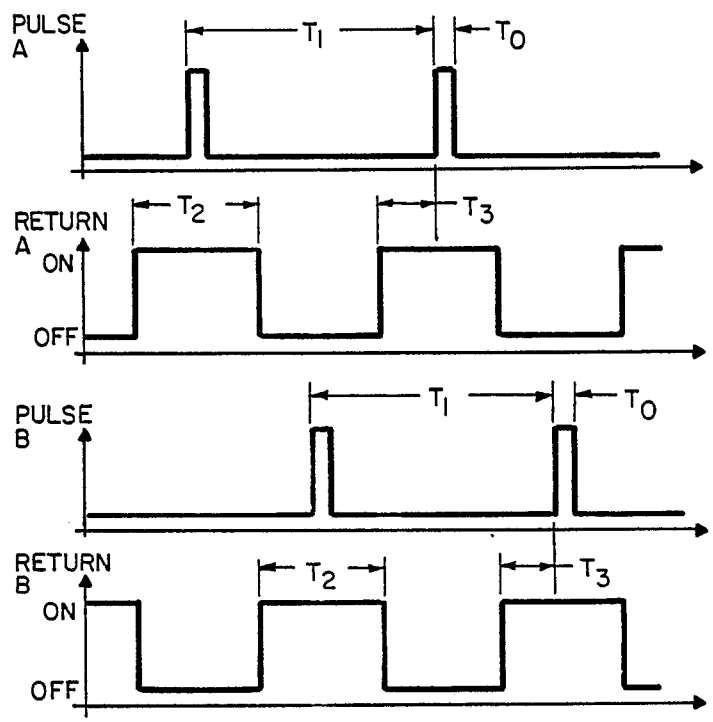
Fig_3
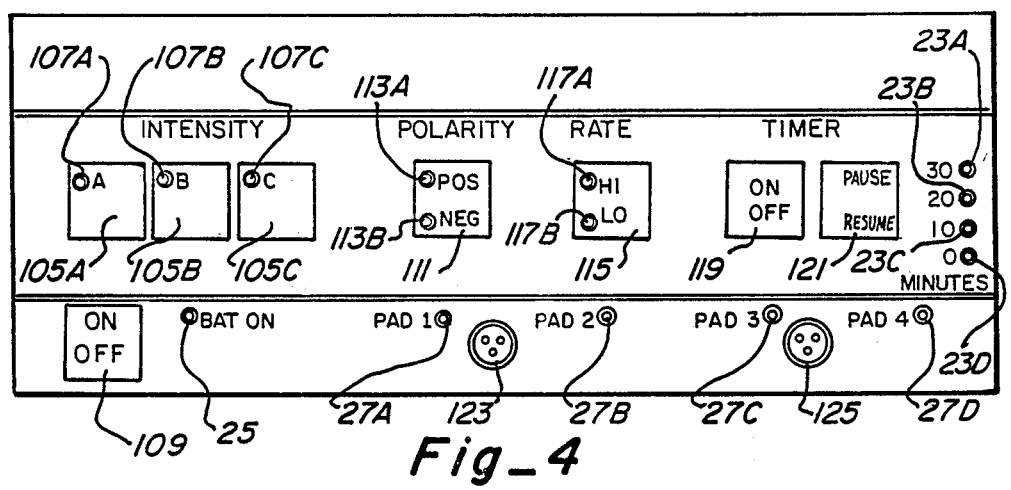
Fig_4

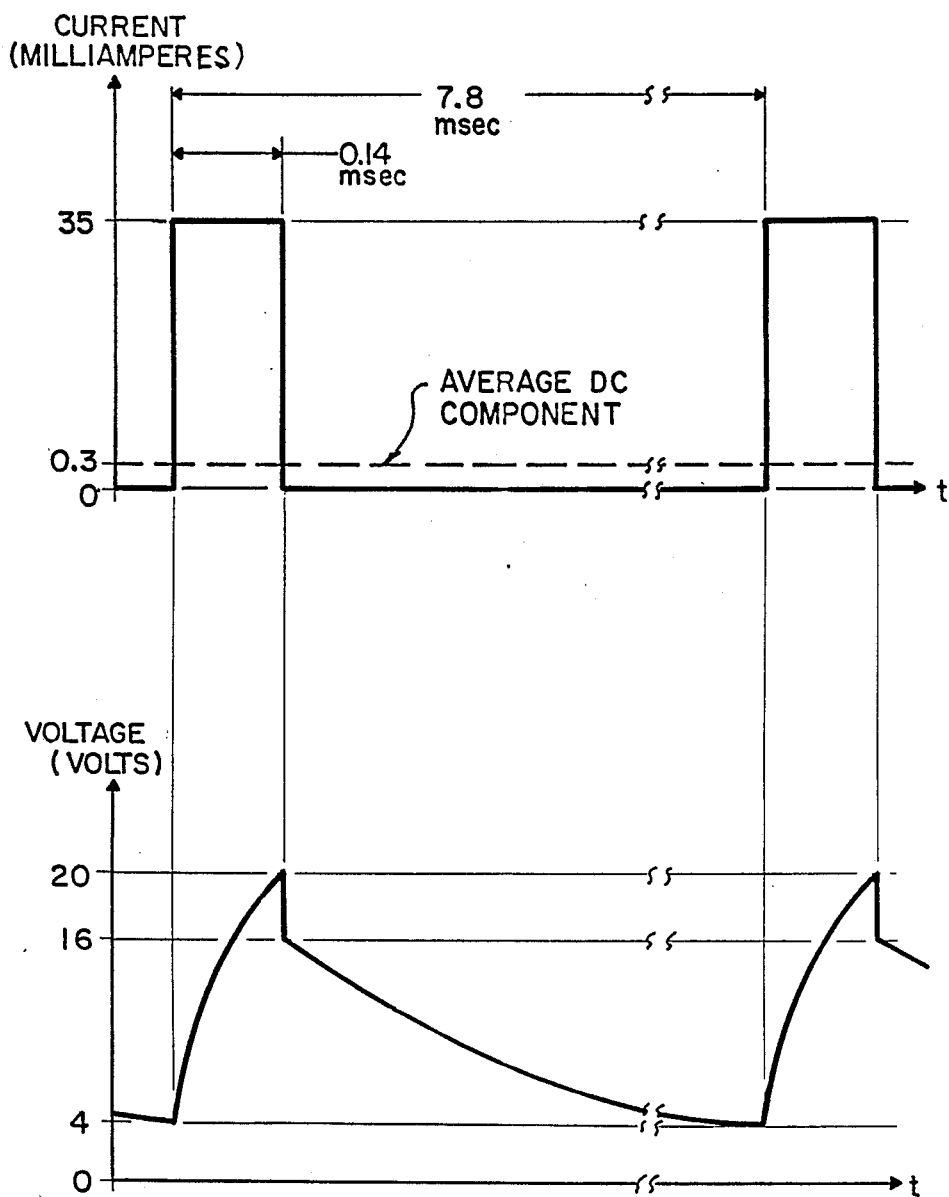
Fig_5

ELECTRONIC STIMULATING DEVICE FOR ENHANCED HEALING OF SOFT TISSUE WOUNDS

FIELD OF THE INVENTION

This invention relates to an electronic stimulating device, and, more particularly, to such a device for enhancing healing of soft tissue wounds.

BACKGROUND OF THE INVENTION

Pulse stimulating devices are well known and such devices have heretofore been utilized for pain suppression (see, for example, U.S. Pat. Nos. 4,014,347, 4,632,117 and 4,640,286).

In addition, pulse stimulating devices have been heretofore suggested for use in treating inflammatory conditions, edema, sprains, muscle spasms, and the like (see, for example, the Vara/Pulse Galvanic Stimulating Unit manufactured and sold by Staodynamics, Inc., Longmont, Colo.).

It has also been heretofore suggested that stimulating units can be utilized for wound healing and extensive experimental work has been accomplished, for example, using the Vara/Pulse Galvanic Stimulating Unit of Staodynamics, Inc..

SUMMARY OF THE INVENTION

This invention provides an electronic stimulating unit for wound healing and, more particularly, for enhancing healing of soft tissue wounds. Stimulating pulses suitable for enhancing wound healing are applied through a plurality of electrodes, which can include two pairs of active electrodes and a pair of return electrodes, with timer means being included to cause treatment to be automatically carried out for a predetermined period of time, and with intensity of applied pulses being visually indicated.

It is therefore an object of this invention to provide an improved electronic stimulating device for enhancing healing of soft tissue wounds.

It is another object of this invention to provide an improved electronic stimulating device for enhancing wound healing utilizing a timer for causing treatment to occur over a predetermined period of time.

It is another object of this invention to provide an improved electronic stimulating device for enhancing wound healing with stimulating pulses being applied through first and second pairs of electrodes and returned through a pair of return electrodes.

It is still another object of this invention to provide an improved electronic stimulating device for enhancing wound healing wherein the intensity of applied pulses is visually indicated.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 3 is a series of timing waveforms illustrating operation of the electronic stimulating unit shown in FIGS. 1 and 2;

FIG. 4 is a front view illustrating an alternate embodiment of the electronic stimulating unit; and FIG. 5 is a typical representation of current and voltage output waveforms obtained in operation of the electronic stimulating unit described and shown in FIGS. 1 through 4.

DESCRIPTION OF THE INVENTION

Figure 1:
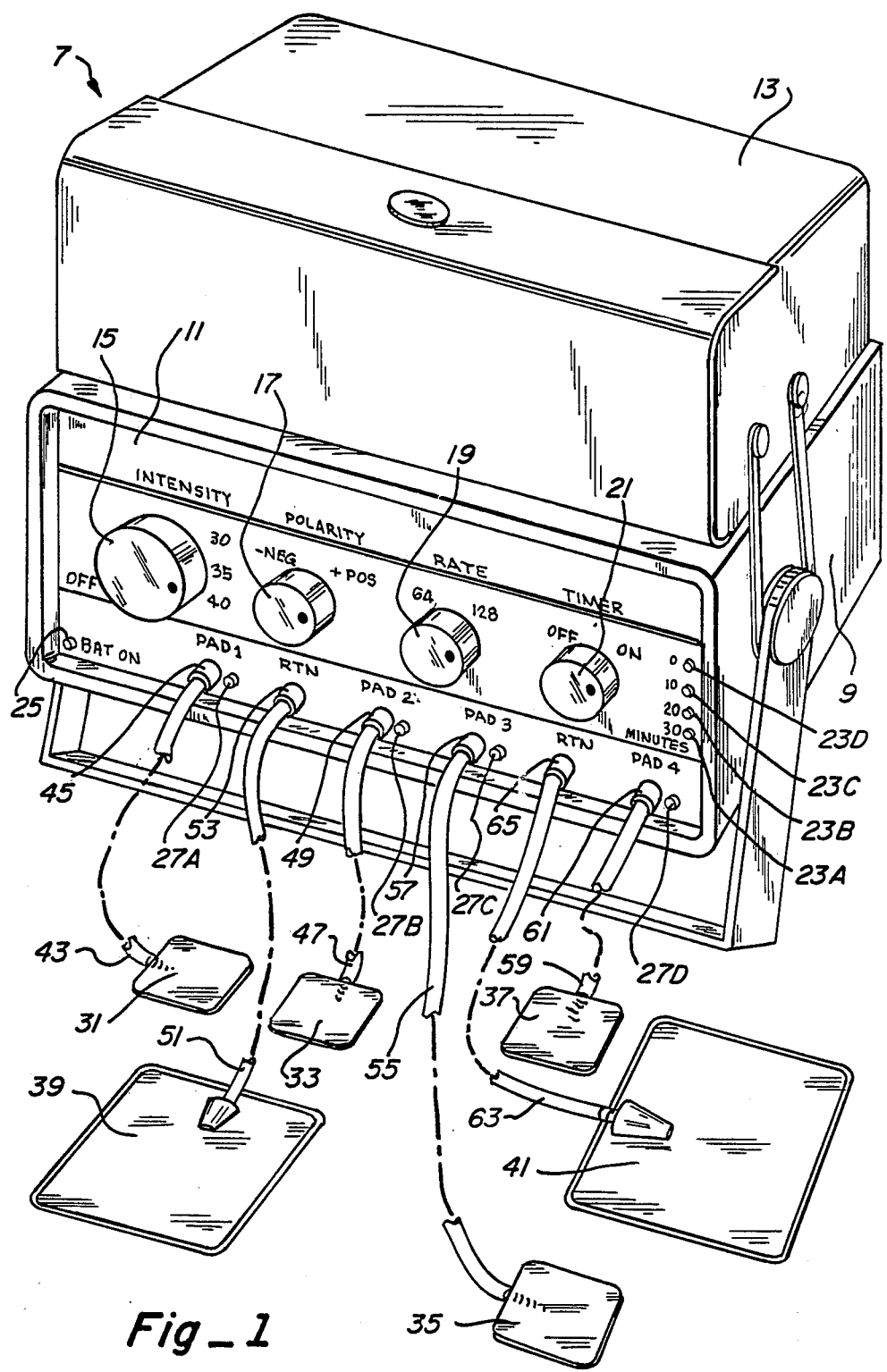
FIG. 1 is a perspective view of an electronic stimulating unit for enhancing wound healing, and illustrating a plurality of electrodes connected therewith.

Electronic stimulating device, or unit, 7 is shown in FIG. 1 as a self-contained portable unit with the entire unit being enclosed within housing 9 and with all operator actuatable controls being accessible at front panel 11. As shown, a carrying case 13 is also preferably provided and includes storage for leads, electrodes, accessories, and the like.

As also shown in FIG. 1, a combined off/on and intensity control knob 15 is provided at the front panel with operable intensities of 30, 35 or 40 ma being preferably only those identified. Polarity knob 17 is provided at front panel 11 with this knob being preferably positionable to provide either negative or positive polarity of pulses. Pulse rate knob 19 is also provided at front panel 11 and preferably allows only selection of a pulse rate of 64 pulses per second (pps) or 1128 pps.

Timer knob 21 is also provided at front panel 11, and, when on, causes initiation of treatment for a predetermined period of time, preferably thirty minutes as illustrated. As shown at front panel 11, when the timer is initially turned on, a treatment time remaining of 30 minutes is indicated by light emitting diode (LED) 23A. As the treatment time progresses, the passage of ten minutes (i.e., a remaining treatment time of twenty minutes) is indicated by LED 23B. In like manner, ten minutes left of the treatment time is indicated by LED 23C, and expiration of the treatment time is indicated by LED 23D. At the end of the treatment time, the timer causes the device to automatically terminate delivery of pulses to the electrodes and hence to the patient being treated.

As also illustrated in FIG. 1, a visual indicator 25 (LED) is used to indicate that the unit is then powered (i.e., battery on), and current indicators (LEDs) 27A, 27B, 27C and 27D are used to indicate delivery of pulses from the unit to each of the electrodes, with the brightness of indicators 27 being visually indicative of the amount of current being delivered.

As also illustrated in FIG. 1, the output pulses from each pulse generator are delivered through first and second pairs 31–33 and 35–37 of active electrodes, or pads, with a return being provided by a pair 39–41 of return electrodes, or pads. As shown, each electrode is separately connected to the stimulating device through connections, or jacks, at front panel 11 with electrode 31 being connected to the device through lead 43 and jack 45, with electrode 33 being connected to the device through lead 47 and jack 49, and with return electrode 39 being connected to the device through lead 51 and jack 53.

In like manner, the second pair of active electrodes 35-37 are connected to the stimulating device with electrode 35 being connected to the device through lead 55 and jack 57, with electrode 37 being connected to the device through lead 59 and jack 61, and with return electrode 41 being connected with the device through lead 63 and jack 65.

Figure 2:
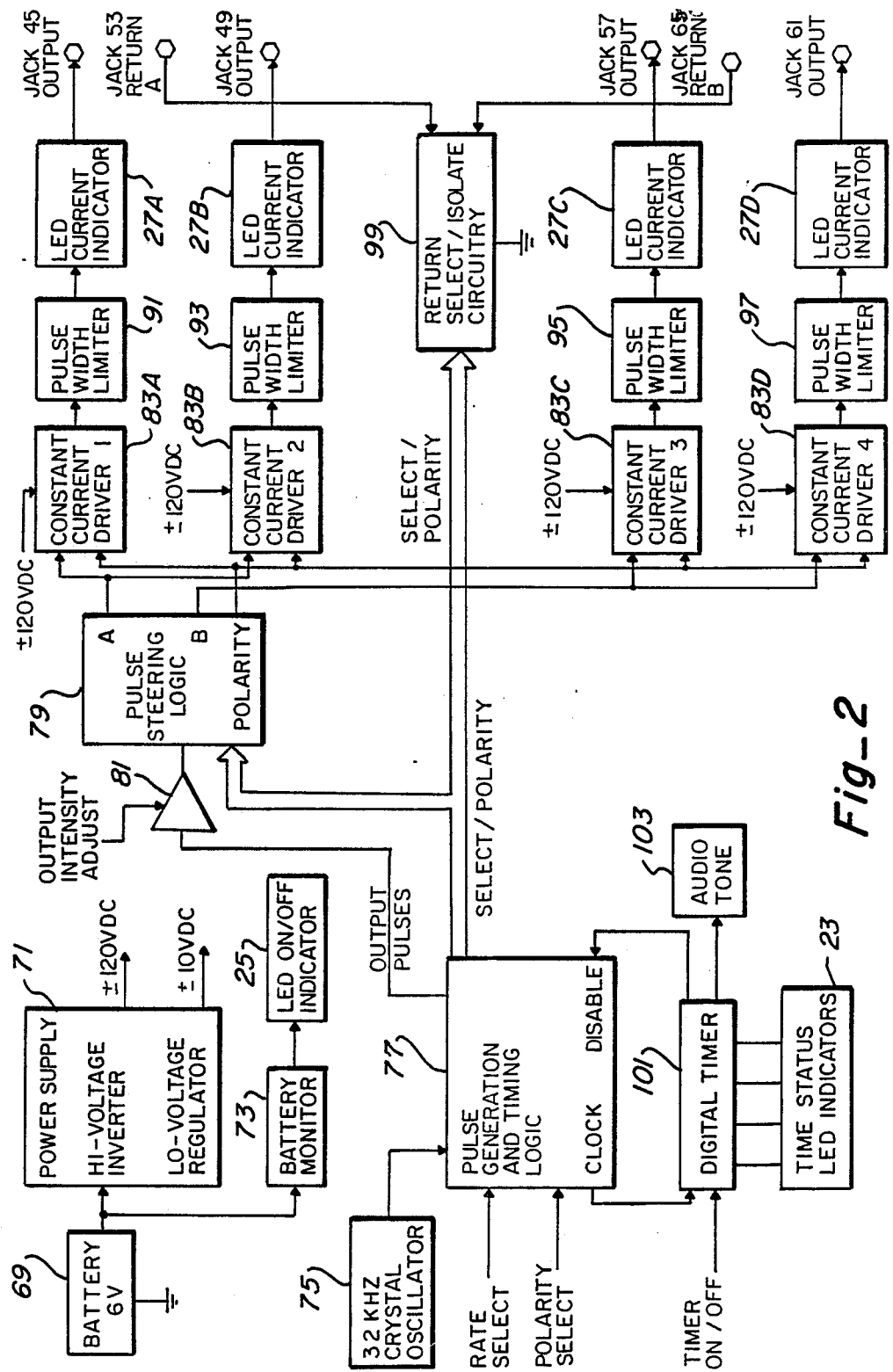
FIG. 2 is a block diagram of the electronic stimulating unit shown in FIG. 1.

A functional block diagram for the stimulating device is illustrated in FIG. 2. As shown, power for the unit is provided by means of battery (6 volt battery) 69 which is connected with high voltage inverter unit 71 to provide a high voltage output (±120 volt DC) and a low voltage of about +10 volt DC for powering the components of the unit. A battery monitor 73 is also provided and is connected with LED on/off indicator 25. Under low battery conditions, battery monitor 73 causes LED 25 to blink to indicate a low battery power level.

Crystal oscillator 75 (operating at about 32 kHz, preferably at 32.768 kHz) provides a time base for generation of pulse and timing signals by pulse generation and timing logic unit 77. Use of crystal based time reference provides accurate timing of output signals (pulse width and rate) which is relatively unaffected by variation in temperature and battery voltage. Pulse generation and timing logic unit 77 selects the rate and polarity of output pulses to be supplied, with the rate and polarity being selected by operator actuation of the controls accessible at the front. While not specifically shown, it is to be realized that a conventional CMOS digital frequency divider can be utilized to provide the basic 64 and 128 pulse per second output pulses by counting down the 32 kHz input frequency.

The select/polarity output from pulse generation and timing logic unit 77 is coupled to pulse steering logic unit 79, and the output pulses are coupled to pulse steering logic unit 79 through output intensity adjust circuit 81. Pulse steering logic unit 79 provides A and B outputs to constant current drivers 83A, 83B, 83C and 83D, and in addition, a polarity output is provided to each of the constant current drivers. Steering logic unit 79 alternately applies control pulses A to drivers 83A and 83B or control pulses B to drivers 83C and 83D.

The output from constant current driver 83A is coupled through pulse width limiter 91 and LED current indicator 27A to jack 45 (connectable with electrode 31). The output from constant current driver 83B is coupled through pulse width limiter 93 and LED current indicator 27B to jack 49 (connectable with electrode 33). The output from constant current driver 83C is coupled through pulse width limiter 95 and LED current indicator 27C to jack 57 (connectable with electrode 35). The output from constant current driver 83D is connected through pulse width limiter 97 and LED current indicator 27D to jack 61 (connectable with electrode 37).

As also indicated in FIG. 2, return electrodes 39 and 41 are connected through return jacks 53 and 65 to the return select/isolate circuitry 99 which is connected with pulse generation and timing logic unit 77. Current return electrodes 39 and 41 are electronically switched and staggered in time to achieve isolation.

The presentation of typical pulses to the various current drivers is indicated, as well as the return therefrom, is indicated in FIG. 3. The relationship of the timing control signals is as follows:

| SELECT RATE | (MILLISECONDS) | | | |
|---|---|---|---|---|
| | T0 | T1 | T2 | T3 |
| 64 | 0.14 | 15.6 | 7.8 | 3.9 |
| 128 | 0.14 | 7.8 | 3.9 | 1.95 |

As also indicated in FIG. 2, a digital timer 101 is connected with pulse generation and timing logic unit 77 with the timer on/off knob 21 being accessible at the front panel, as brought out hereinabove. The time status LED indicators 23 (A through D) are connected with the digital timer, as is an audio tone circuit 103 to allow an audible tone to be generated.

Continuous (or uninterrupted) output pulses can be generated with front panel timer control 21 in the off position by rotating the off/on and intensity knob 15 clockwise. If the digital timer is utilized to cause patient treatment, timer control 21 is switched to the on position (the off/on and intensity knob 15 must also be rotated clockwise to power the device) and 8 hz clock pulses are applied to a CMOS digital frequency divider operating as the timer.

Initially the 30 minute time remaining LED 23A on the front panel will be energized indicating the time of treatment remaining. After 10 minutes, the 20 minute time remaining indicator LED 23B will be energized, and after 20 minutes, the 10 minute time remaining LED 23C will be energized. After 30 minutes of elapsed treatment time, the zero indicator LED 23D will be energized and tone generator 103 will sound for approximately 10 seconds notifying the user that the 30 minute treatment time has elapsed.

At the end of the timed treatment time, a logic disable signal is also simultaneously provided to the pulse generation circuitry and this terminates output pulses to the patient. To reset the timer, the off/on and intensity knob 15 must be rotated counter clockwise until the unit switches off, and then rotated clockwise to again power the unit. This prevents a startle effect by repowering the unit only at minimum output intensities.

As can be appreciated from the foregoing, four identical output driver stages are used in the stimulating unit. Each of the linear constant-current amplifiers is capable of delivering peak current pulses of 45 milliamperes into each treatment pad output. Pulse polarity can be either plus or minus depending on the panel control setting, and pulse output voltage will be a maximum of ±120 volts (under a no load condition). In a typical patient treatment situation with an intensity setting of 30 ma and 2 K ohm electrode system resistance, the pulses will be 60 volts peak.

The pulses generated by each output driver 83A through 83D can be continuously monitored by four passive pulse width limiter circuits 91, 93, 95 and 97. In the event of a single component failure anywhere in the stimulator unit, the pad outlets are electronically shunted by triac clamping devices in the pulse limiters. Charge contained in a single output pulse is effectively limited to 50 microcoulombs under fault conditions.

Four output current indicators 27A-D are located on the front panel adjacent to associated pad jacks of the active electrodes. These LED indicators are bidirectional devices which provide relative indications of treatment current being delivered from each pad output. Brightness will increase proportionally with current, and will operate with either selected polarity. The LEDs will be extinguished completely when no connections are made, and serve as a quick visual assessment of electrode system integrity or patient hook-up.

While various treatment protocols have been suggested for effecting wound healing, it has been found that repeated short treatments of electrical stimulation applied through an active electrode positioned preferably at the wound (and with a dispersive electrode positioned at a distance from the wound) has been effective. In addition, it has been found effective to utilize a treatment cycle that includes application of negative pulses during an initial treatment period (one or more days), followed by application of positive pulses during a second treatment period (one or more days), with the treatment cycle (normally extending for a number of days) being therefore repeated one or more times until healing of the wound is completed. It has also been found effective to utilize a short treatment time (preferably of about 30 minutes) with pulses being applied through the active electrode at an intensity of between about 2.8 and 7.0 coulombs per pulse (and preferably causing constant current pulses having an intensity of between about 30 and 40 ma to be applied), at a rate preferably of 64 pps or 128 pps with the treatment being repeated between about 2 to 4 times a day.

FIG. 4 illustrates the front panel of an alternate embodiment of the stimulating unit of this invention. As shown, the knobs of the earlier described embodiment have been replaced by a plurality of push buttons (preferably of the type allowing momentary contact and enhanced tactile qualities in their use). As shown, push button switches 105A, 105B, and 105C are utilized for selecting intensity and when so utilized, the intensity can only be set by a user at one of three levels (such as, for example, at 30, 35 and 40 milliamp levels).

LEDs 107A-C are provided with each being located on different ones of the push button switches 105A-C respectively to indicate the level of intensity then selected. For example, if the 35 milliamp level is to be selected, the operator will push button 105B and hold it depressed. LED 107B will blink indicating that the output pulse intensity is slowly increasing at a predetermined rate but has not yet reached the 35 milliamp level. Output pulse intensity will continue increasing as long as button 105B is held depressed, and will stop if the button is released (LED 107B will continue to blink). If the 35 milliamp level is reached, LED 107B will be steadily on, and no further increase in the pulse intensity occurs. The process is similar for buttons 105A and 105C. This feature thus allows for patient comfort and accommodation until the proper therapeutic level (intensity) can be achieved. As also shown in FIG. 4, off/on push button switch 109 is also provided for turning the unit off and on (with on being indicated by energization of LED 25 as battery on).

A push button polarity switch 111 is also utilized for selecting positive and negative polarities with LEDs 113A and B indicating which polarity has then been selected. Likewise, a rate select push button 115 is used with LEDs 117A and B indicating one of two rates selected, either high or low (which rates could be 64 pps and 128 pps, for example). When either button 111 or button 115 is pushed for a polarity or rate change during operation, there will be a "soft" gradual change of the output over several seconds from one polarity to the other, or from one pulse rate to the other, as the case may be, thereby avoiding abrupt changes which may startle a patient/user.

A push button off/on timer switch 119 is used with LEDs 23A through D indicating the time of treatment remaining, and a pause and resume push button switch 121 is also included to allow the timing to be interrupted for a short period of time and then resumed. While in the pause mode the activated LED 23 will blink, thus indicating a pause in timing. Jacks 123 and 125 are each used to connect a pair of active electrodes and a return electrode to the unit, with LED current indicators 27A-D being utilized to indicate delivery of pulses to each active electrode.

The unit shown in FIG. 4 operates in the same manner as that shown above in FIGS. 1 through 3. However, while not specifically shown, it is to be realized that the unit shown in FIG. 4 could effectively be utilized with a suitable conventional microprocessor.

FIG. 5 illustrates typical current and voltage output waveforms obtained in operation of the unit described in FIGS. 1 through 4 under a typical patient load and operating at the 35 ma intensity and the 128 pps rate. As indicated, the pulses are spaced approximately 7.8 milliseconds (ms) from one another at the 128 pps rate (at the 64 pps rate the pulse spacing would be approximately 15.6 ms), with a current peak duration of approximately 0.14 ms. As illustrated, the output includes both a pulsed component and a galvanic DC component, which are believed effective in combination to promote wound healing. The voltage output pulses peak at approximately 20 volts, returning to a minimum voltage of approximately 4 volts between pulses.

As can be appreciated from the foregoing, this invention provides an improved stimulating device for enhancing healing of soft tissue wounds.

What is claimed is:

1. An electronic stimulating device for enhancing healing of soft tissue wounds, said device comprising:
   signal generating means providing a stimulating signal suitable for enhancing healing of soft tissue, said stimulating signal having a peak current not greater than about 40 ma;
   electrode means connected with said generating means for receiving said stimulating signal therefrom, said electrode means being adapted to be positioned contiguous to said soft tissue wound to be healed;
   return electrode means adapted to be positioned adjacent to said soft tissue wound to be healed; and
   control means connected with said signal generating means for controlling application of said stimulating signal to said soft tissue wound, said control means including timer means for causing application of said stimulating signal to said soft tissue wound for a predetermined time period.

2. The device of claim 1 wherein said control means includes pulse generating means for generating control pulses for application to said signal generating means for controlling application of said stimulating signal to said soft tissue, said timer means being connected with said pulse generating means.

3. The device of claim 2 wherein said timer means includes a timer connected with said signal generating means and indicating means connected with said timer for indicating a factor of time of treatment.

4. The device of claim 3 wherein indicating means includes at least one of visual indicating means and audible indicating means.

5. The device of claim 3 wherein said indicating means includes visual indicating means capable of indicating the remaining time of treatment as said factor of time of treatment.

6. The device of claim 1 wherein said timing means is adapted to provide for application of said stimulating signal to said soft tissue for a time period of about 30 minutes.

7. The device of claim 1 wherein said control means includes switching means for enabling power to be applied to said device, wherein said timer means includes an on/off control, wherein said timer means is inoperable except when said device is powered on by said switching means and said on/off control is in the on position, and wherein said timer means is connected with said switching means in a manner such that said timing means is precluded from terminating application of said stimulating signal by said device if said on/off control is actuated from the on position to the off position during a timing period.

8. The device of claim 1 wherein said device includes intensity indicative means connected with said signal generating means, the intensity of said intensity indicative means being indicative of the intensity of said stimulating signal.

9. An electronic stimulating device for enhancing healing of soft tissue wounds, said device comprising:
first and second pairs of signal generating means each of which provides a stimulating signal suitable for enhancing healing of soft tissue wounds;
first and second pairs of electrodes each of which is connected with a different one of said first and second pairs of signal generating means to receive said stimulating signals therefrom, said electrodes being adapted for positioning contiguous to a soft tissue wound to be healed;
first and second return electrodes adapted to be positioned adjacent to said soft tissue wound to be healed;
control means for controlling application of said stimulating signals to said soft tissue wound through said first and second pairs of electrodes; and
first and second indicating means connected with said first and second pairs of signal generating means, the intensity of said indicating means being indicative of the intensity of said stimulating signals provided by said first and second pairs of said signal generating means.

10. The device of claim 9 wherein said control means includes pulse generating means connected with said first and second pairs of signal generating means for providing pulsed output signals thereto as said stimulating signals.

11. The device of claim 9 wherein said control means includes timing means providing a timed treatment application of said stimulating signal to said soft tissue wound.

12. The device of claim 9 wherein said control means includes switching means for enabling power to be applied to said device, wherein said timer means includes an on/off control, wherein said timing means is inoperable except when said device is powered on by said switching means and said off/on control is in the on position, and wherein said timer means is connected with said switching means in a manner such that said timing means is precluded from terminating application of said stimulating signal by said device if said on/off control is changed to the off position during a timing period.

13. An electronic stimulating device for enhancing healing of soft tissue wounds, said device comprising:
first and second pairs of constant current devices providing constant current output pulses, said constant current pluses having a peak current not greater than about 40 ma;
first and second pairs of visual indicating means connected with said first and second pairs of constant current devices, the intensity of said visual indicating means being indicative of the intensities of said constant current output pulses;
first and second pairs of electrodes each pair of which is connected to a different pair of said first and second pairs of constant current devices, said electrodes being adapted to be positioned contiguous to a soft tissue wound to be healed and to receive said constant current output pulses from said first and second pairs of constant current devices;
first and second return electrodes adapted to be positioned adjacent to said soft tissue wound to be healed;
isolation means connected with said return electrodes;
power supply means for supplying a predetermined high voltage to said first and second pairs of constant current devices;
pulse generating means for providing a series of control pulses, said pulse generating means being connected with said constant current devices to control operation of the same whereby each of said constant current devices produces said constant current output pulses for healing of said soft tissue wounds;
intensity control means connected with said pulse generating means, said intensity control means including an on/off switch for powering said device on and off; and
timer means connected with said pulse generating means for enabling treatment by said stimulating pulses over a predetermined timed period, said timer means being connected with said intensity control means whereby operation of said timer means during said timed period can be terminated only by actuation of said on/off switch of said intensity control means from the on position to the off position.

14. The device of claim 13 wherein said device includes pulse limiting means connected with said first and second pairs of constant current devices.

15. The device of claim 13 wherein said timer means is a digital timer.

16. The device of claim 13 wherein said device includes polarity switching means connected with said first and second pairs of constant current devices.

17. The device of claim 16 wherein said device includes pulse rate selection means, and wherein polarity and rate changes of said output pulses effected during operation of said device by switching said polarity switching means and selection at said pulse rate selection means are gradually effected.

18. The device of claim 13 wherein said intensity control means includes switching means for switching the intensity of said applied stimulating pulses and wherein changes in intensity of said applied stimulating pulses are gradually effected.

19. The device of claim 13 wherein said device includes pause/resume switching means connected with said timer means.

20. The device of claim 13 wherein said first and second pairs of constant current devices provide output pulses having pulses and galvanic components.

* * * * *